United States Patent
Miller (10) Patent No.: US 9,421,349 B2
(45) Date of Patent: Aug. 23, 2016

(54) ANGIOPLASTY PRESSURE TRANSDUCER

(71) Applicant: Stuart H. Miller, Clifton, NJ (US)

(72) Inventor: Stuart H. Miller, Clifton, NJ (US)

( * ) Notice: Subject to any disclaimer, the term of this patent is extended or adjusted under 35 U.S.C. 154(b) by 787 days.

(21) Appl. No.: 13/739,312

(22) Filed: Jan. 11, 2013

(65) Prior Publication Data

US 2013/0190797 A1 Jul. 25, 2013

Related U.S. Application Data

(60) Provisional application No. 61/586,016, filed on Jan. 12, 2012.

(51) Int. Cl.

| A61B 5/021 | (2006.01) |
|---|---|
| A61M 29/02 | (2006.01) |
| A61B 5/02 | (2006.01) |
| A61B 5/0215 | (2006.01) |
| A61B 5/00 | (2006.01) |

(52) U.S. Cl.
CPC ............ *A61M 29/02* (2013.01); *A61B 5/02007* (2013.01); *A61B 5/0215* (2013.01); *A61B 5/02141* (2013.01); *A61B 5/4848* (2013.01)

(58) Field of Classification Search
CPC .............. A61B 5/02141; A61B 5/205; A61B 5/0215–5/02158; G01L 7/08–7/088; A61N 5/1002; A61N 5/1015; A61N 5/1016
USPC .......... 600/1–8, 485, 486, 488; 606/192, 193, 606/195
See application file for complete search history.

(56) References Cited

U.S. PATENT DOCUMENTS

| 3,435,819 A | 4/1969 | Reynolds et al. |
|---|---|---|
| 3,648,687 A | 3/1972 | Ramsey, III |
| 3,720,201 A | 3/1973 | Ramsey, III |
| 4,036,216 A | 7/1977 | Ramsey, III |
| 4,262,529 A | 4/1981 | Rosenblatt et al. |
| 4,840,068 A | 6/1989 | Mayhew, Jr. |
| 4,901,731 A | 2/1990 | Millar |
| 4,920,972 A | 5/1990 | Frank et al. |
| 4,953,553 A | 9/1990 | Tremulis |
| 5,178,153 A | 1/1993 | Einzig |
| 5,209,726 A * | 5/1993 | Goosen ................. A61M 25/00 604/265 |
| 5,263,962 A * | 11/1993 | Johnson ................ A61M 29/02 600/115 |

(Continued)

OTHER PUBLICATIONS

"Practical Stress Analysis in Engineering Design" by R. Huston & H. Josephs, (pages (pp. 529-530).

*Primary Examiner* — Catherine B Kuhlman
(74) *Attorney, Agent, or Firm* — Welsh Flaxman & Gitler LLC (57) ABSTRACT

An angioplasty pressure transducer includes a cylindrical member defining an inner cavity. The first end of the cylindrical member is provided with a fluid port allowing the passage of fluid into and out of the cylindrical member due to pressure changes in the physiological fluid being monitored. The angioplasty pressure transducer also includes a cylindrical elastomeric sleeve surrounding the cylindrical member. A cylindrical, transparent housing member is positioned about the cylindrical member such that a substantial portion of the outer surface of the cylindrical member, as well as the elastomeric sleeve, are enclosed and encased within the housing member. The cylindrical wall includes a plurality of small apertures spaced cylindrically about the circumference of cylindrical wall at a position substantially located at the longitudinal center of the cylindrical member, the apertures permitting pressurized fluid to pass between the inner cavity and the outer surface of the cylindrical member.

17 Claims, 6 Drawing Sheets

(56) References Cited

U.S. PATENT DOCUMENTS

| | | |
|---|---|---|
| 5,792,959 A | 8/1998 | Marchant |
| 6,139,523 A | 10/2000 | Taylor et al. |
| 6,167,763 B1 | 1/2001 | Tenerz et al. |
| 6,371,937 B1 | 4/2002 | McPhee |
| 6,491,619 B1 * | 12/2002 | Trauthen .............. A61K 9/1641 257/E21.058 |
| 6,767,637 B2 | 7/2004 | Park et al. |
| 7,458,980 B2 | 12/2008 | Barbut |
| 7,524,274 B2 * | 4/2009 | Patrick ................. A61N 5/1015 600/1 |
| 7,635,376 B2 | 12/2009 | Barbut |
| 2006/0129175 A1 * | 6/2006 | Griffin ............. A61B 17/22032 606/192 |
| 2011/0098602 A1 * | 4/2011 | Campbell ............ A61B 5/1076 600/587 |

* cited by examiner

FIG. 10  Pressure Transducer Design for Angioplasty $D := 1 \quad d := .5, .51 ... .99 \quad E := 30 \quad P := 2.93 \quad v := .499 \quad L := 1$ $$k(d) := \frac{d}{D} \qquad \delta(d) := \frac{P \cdot D \cdot (2 - v) \cdot (1 + k(d))^2}{16 \cdot E \cdot (1 - k(d))}$$

| k(d)= | δ(d)= |
|---|---|
| 0.5 | 0.041 |
| 0.51 | 0.043 |
| 0.52 | 0.044 |
| 0.53 | 0.046 |
| 0.54 | 0.047 |
| 0.55 | 0.049 |
| 0.56 | 0.051 |
| 0.57 | 0.053 |
| 0.58 | 0.054 |
| 0.59 | 0.056 |
| 0.6 | 0.059 |
| 0.61 | 0.061 |
| 0.62 | 0.063 |
| 0.63 | 0.066 |
| 0.64 | 0.068 |
| 0.65 | 0.071 | where:

D = Tube OD, in d = Tube ID, in

E + tube modulus, psi

P = tube inflation pressure, psi v = tube poisson's ratio

$\delta(d)$ = radial tube growth in the region not affected by the end closures, in Note: a 20 durometer rubber has a tangent modulus of approximately 30 psi at an elongation of 20% "Engineering uses of rubber page 69"

Radial tube growth based on the tube ID

For example
At a value of d=0.8", the elastomeric tube will deforem radially by an amount $\delta(d)$=0.15" into the cavity provided in the transparent portion of the transducer. Since the radial deflection of the elastomer in the dilation region is greater than the value of $\delta(d)$ given above, the radial dimension of region 60 in the patent application should be greater than 0.15",
how much greater is best determined experimentally during the scale marking procedure on the outer portion of the transparent portion 62 in the design stage.

FIG. 11

ANGIOPLASTY PRESSURE TRANSDUCER

CROSS REFERENCE TO RELATES APPLICATION

This application claims the benefit of U.S. Provisional Application Ser. No. 61/586,016, entitled "ANGIOPLASTY PRESSURE TRANSDUCER," filed Jan. 12, 2012.

BACKGROUND OF THE INVENTION

1. Field of the Invention

The present invention relates to a pressure transducer. In particular, the present invention relates to an angioplasty pressure transducer and a method for use.

2. Description of the Related Art

When performing angioplasty it is important to determine whether the procedure has been successful and the stenosis has been fully opened for the flow of blood. Various diagnostic tools exist for performing this function.

However, these diagnostic tools are cumbersome to use, requiring complicated equipment necessitating substantial time and effort to set up and use. In particular, endovascular surgeons rarely use a pressure transducer after angioplasty. The reasons for this lack of use include the cost of available pressure transducers adapted for pressure measurements after angioplasty, the time necessary to calibrate devices available for use in measuring pressure after an angioplasty, and the need for reinsertion of a pressure transducer after angioplasty is time consuming and could cause damage to the vessel. In addition, current pressure transducers require fluoroscopy/x-rays to document placement and the most accurate reading is an "enhanced" reading, that is, after administration of a vasodilator, such as IV Nitroglycerin.

As such, a need exists for a method and apparatus allowing a physician to make a reliable and efficient determination as to the success of an angioplasty.

SUMMARY OF THE INVENTION

It is, therefore, an object of the present invention to provide an angioplasty pressure transducer including a cylindrical member defining an inner cavity. The cylindrical member includes a cylindrical wall having an inner surface and an outer surface, as well as a first end and a second end. The first end of the cylindrical member is provided with a fluid port allowing the passage of fluid into and out of the cylindrical member due to pressure changes in the physiological fluid being monitored. The angioplasty pressure transducer also includes a cylindrical elastomeric sleeve surrounding the cylindrical member such that the cylindrical elastomeric sleeve is wrapped about the outer surface of the cylindrical member. A cylindrical, transparent housing member is positioned about the cylindrical member such that a substantial portion of the outer surface of the cylindrical member, as well as the elastomeric sleeve, are enclosed and encased within the housing member. The cylindrical wall includes a plurality of small apertures spaced cylindrically about the circumference of the cylindrical wall at a position substantially located at the longitudinal center of the cylindrical member, the apertures permitting pressurized fluid to pass between the inner cavity and the outer surface of the cylindrical member.

It is also an object of the present invention to provide an angioplasty pressure transducer wherein the cylindrical member further includes a removable stopper at the second end thereof.

It is another object of the present invention to provide an angioplasty pressure transducer wherein the cylindrical member is composed of a substantially rigid plastic.

It is a further object of the present invention to provide an angioplasty pressure transducer wherein the fluid port includes a central passageway for permitting fluid communication between the inner cavity of the cylindrical member and the external environment.

It is also an object of the present invention to provide an angioplasty pressure transducer wherein the fluid port includes a coupling mechanism for selective and secure attachment to a catheter, or other cannula.

It is another object of the present invention to provide an angioplasty pressure transducer wherein the stopper is shaped and dimensioned for frictionally mounting within an opening at the second end of cylindrical member.

It is a further object of the present invention to provide an angioplasty pressure transducer wherein the elastomeric sleeve provides a barrier for the passage of fluid from within the inner cavity and creates an external cavity, or volume, into which fluid passes when pressure within the inner cavity forces the fluid through the apertures formed in the cylindrical wall of the cylindrical member and into the external cavity as defined by the outer surface of the cylindrical member and the elastomeric sleeve.

It is also an object of the present invention to provide an angioplasty pressure transducer wherein the elastomeric sleeve is a resilient, cylindrical member.

It is another object of the present invention to provide an angioplasty pressure transducer wherein the elastomeric sleeve is shaped and dimensioned to fit snugly about the outer surface of the cylindrical member when no pressure is being applied.

It is a further object of the present invention to provide an angioplasty pressure transducer wherein the elastomeric sleeve includes an open first end and an open second end with a central segment connecting the first end and the second end.

It is also an object of the present invention to provide an angioplasty pressure transducer wherein the first end of the elastomeric sleeve is coupled to the outer surface of the cylindrical member adjacent the first end of the cylindrical member thereof and the second end of the elastomeric sleeve is coupled to the outer surface of the cylindrical member adjacent the second end of the cylindrical member.

It is another object of the present invention to provide an angioplasty pressure transducer wherein the central segment of the elastomeric sleeve is not secured to the outer surface of the cylindrical member.

It is a further object of the present invention to provide an angioplasty pressure transducer wherein the transparent housing member includes a cylindrical wall having an inner surface and an outer surface. The transparent housing member also includes a first end and a second end, wherein the inner surface of the transparent housing member faces the elastomeric sleeve and outer surface of the cylindrical wall of the cylindrical member, while the outer surface of the transparent housing member faces the external environment.

It is also an object of the present invention to provide an angioplasty pressure transducer wherein the first end of the transparent housing member is provided with an inwardly facing annular coupling flange and the second end of the transparent housing member is provided with inwardly facing annular coupling flange, the inwardly facing annular coupling flanges extending from the cylindrical wall of the transparent housing member, which contact and are secured to the outer surface of the cylindrical member with the elastomeric sleeve secured therebetween.

It is another object of the present invention to provide an angioplasty pressure transducer wherein the cylindrical wall of the transparent housing member is spaced from the outer surface of the cylindrical wall of the cylindrical member defining a central cavity that is defined by the inner surface of the cylindrical wall, the inwardly facing annular coupling flange at the first end of the transparent housing member, the inwardly facing annular coupling flange at the second end of the transparent housing member, and the outer surface of the cylindrical wall.

It is a further object of the present invention to provide an angioplasty pressure transducer wherein the transparent housing member includes air bleed holes to prevent trapping air in the inside of the transparent housing member as the pressure in the angioplasty pressure transducer increases.

It is also an object of the present invention to provide an angioplasty pressure transducer wherein the transparent housing member is provided with a calibrated graduated scale.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

In accordance with the present invention, and with reference to FIGS. 1 to 9, an angioplasty pressure transducer 10 is disclosed. The angioplasty pressure transducer 10 is designed to detect whether or not a vascular stenosis, or narrowing, has been successfully treated without subjecting the patient to additional radiation or intravenous contrast dye.

Figure 1:
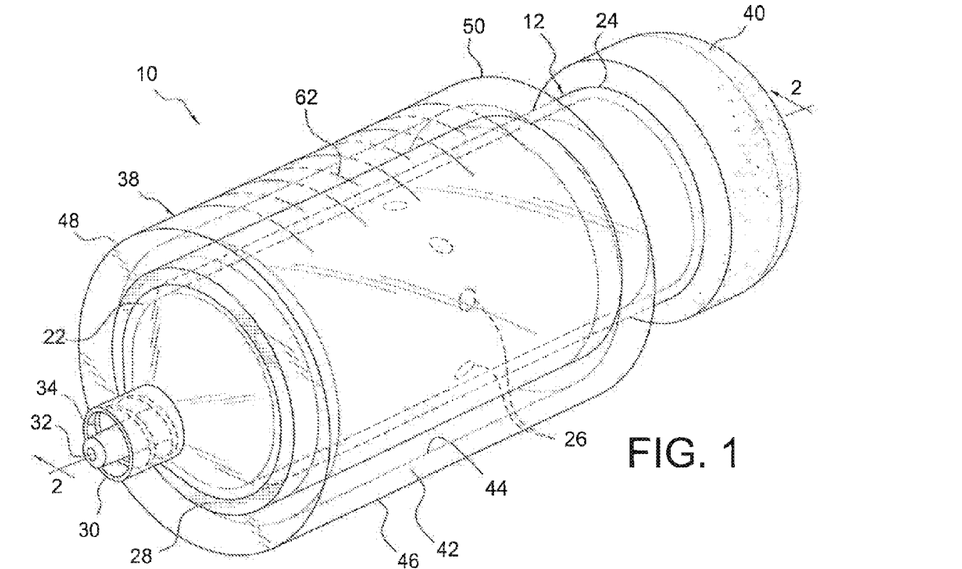
FIG. 1 is a perspective view of an angioplasty pressure transducer in accordance with the present invention.
Figure 2:
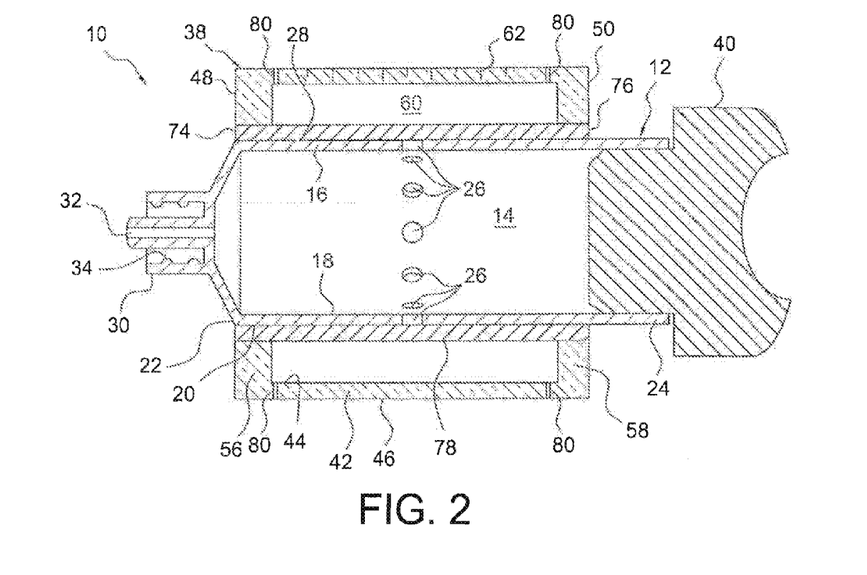
FIG. 2 is a cross sectional view along the line 2-2 of the angioplasty pressure transducer shown in FIG. 1, with the application of no pressure as discussed below.

Referring to FIGS. 1 and 2, the innermost portion of the angioplasty pressure transducer 10 is composed of a cylindrical member 12 defining an inner cavity 14. The cylindrical member 12 is composed of a substantially rigid plastic. It is appreciated various plastics used in the manufacture of medical instruments may be employed. The cylindrical member 12 includes a cylindrical wall 16 having an inner surface 18 and an outer surface 20. The cylindrical member 12 also includes a first end 22 and a second end 24. It is appreciated the cylindrical member 12 resembles a standard syringe complete with removable stopper 40 at the second end 24 thereof.

As will be appreciated based upon the following disclosure, cylindrical wall 16 is provided with a plurality of small apertures 26 spaced in a cylindrical pattern about the circumference of cylindrical wall 16 at a position substantially located at the longitudinal center of the cylindrical member 12. Although the small apertures are located at a position substantially at the longitudinal center of the cylindrical member in accordance with a preferred embodiment, it is appreciated the small apertures may also be positioned at an off-center location. The apertures 26 permit the pressurized fluid within the angioplasty pressure transducer 10 to pass between the inner cavity 14 and the outer surface 20 of the cylindrical member 12 so as to deflect a solid, cylindrical elastomeric sleeve 28 surrounding the cylindrical member 12, in the radial direction.

The first end 22 of the cylindrical member 12 is provided with a fluid port 30 allowing the passage of fluid into and out of the cylindrical member 12 due to pressure changes in die physiological fluid being monitored. In accordance with a preferred embodiment, the fluid port 30 is a standard luer lock commonly used in conjunction with medical devices requiring the selective connection of various components required to be maintained in fluid communication. It is, however, appreciated other connection structures used in fluid connection of medical instruments may be employed. As such, and as discussed below in greater detail, a catheter, or other cannula, for example, a needle, positioned within the body of a patient may be selectively secured to the present angioplasty pressure transducer 10 for fluid communication with the inner cavity 14 of the cylindrical member 12. It is appreciated the present fluid port 30 includes both a central passageway 32 for permitting fluid communication between the inner cavity 14 of the cylindrical member 12 and the external environment and a coupling mechanism 34 for selective and secure attachment to a catheter, or other cannula, that might be attached to the cylindrical member 12.

As briefly discussed above, the angioplasty pressure transducer 10 is provided with a selectively attachable stopper 40 for positioning at the second end 24 of the cylindrical member 12. The stopper 40 is, therefore, shaped and dimensioned for frictionally mounting within the opening defined at the second end 24 of cylindrical member 12. As such, and as will be appreciated based upon the functionality of the present angioplasty pressure transducer 10 as discussed below, the inner cavity 14 may be effectively closed for performing pressure measurements. The stopper 40 is preferably manufactured from a resilient material. It is appreciated the resilient material is selected such that the stopper 40 may be penetrated by a needle for accessing the inner cavity 14 from the external environment and reseated after the needle is removed therefrom.

The elastomeric sleeve 28 is wrapped about the outer surface 20 of the cylindrical member 12. As will be appreciated, the elastomeric sleeve 28 provides a barrier for the passage of fluid from within the inner cavity 14 and creates an external cavity, or volume, 36 into which fluid passes when pressure within the inner cavity 14 (as generated based upon pressures measured within a patient) forces the fluid through the apertures 26 formed in the cylindrical wall 16 of the cylindrical member 12 and into an external cavity 36 defined by the outer surface 20 of the cylindrical member 12 and the elastomeric sleeve 28 (see FIGS. 3 and 4). However, and in contrast to the inner cavity 14 which has a definite volume due to the substantially rigid nature of the cylindrical member 12, the volume of the external cavity 36 as defined by the outer surface 20 and the elastomeric sleeve 28 will vary depending upon the pressure of the fluid being forced from within the inner cavity 14.

The elastomeric sleeve 28 is a resilient, cylindrical member and is shaped and dimensioned to fit snugly about the outer surface 20 of the cylindrical member 12, when no pressure is being applied. As such, the elastomeric sleeve 28 includes an open first end 74 and an open second end 76 with a central segment 78 connecting the first end 74 and the second end 76. The first end 74 of the elastomeric sleeve 28 is coupled to the outer surface 20 of the cylindrical member 12 adjacent the first end 22 of the cylindrical member 12 thereof and the second end 76 of the elastomeric sleeve 28 is coupled to the outer surface 20 of the cylindrical member 12 adjacent the second end 24 of the cylindrical member 12. The central segment 78 of the elastomeric sleeve 28 is not secured to the outer surface 20 of the cylindrical member 12 and, therefore, may move away from the outer surface 20 as discussed below.

A substantial portion of the outer surface 20 of the cylindrical member 12, as well as the elastomeric sleeve 28, are enclosed and encased within a cylindrical, transparent housing member 38 positioned about the cylindrical member 12. As shown in FIG. 1, the cylindrical member 12 and transparent housing member 38 are concentric. It is appreciated the transparent housing member may be made from various clear plastics employed in the manufacture of medical instruments.

As with the cylindrical member 12, the transparent housing member 38 includes a cylindrical wall 42 (however, in the case of the transparent housing member 38, the cylindrical wall 42 is solid and includes only apertures 80 for venting purposes as discussed below in greater detail) having an inner surface 44 and an outer surface 46. The transparent housing member 38 also includes a first end 48 and a second end 50. The inner surface 44 of the transparent housing member 38 faces the elastomeric sleeve 28 and outer surface 20 of the cylindrical wall 16 of the cylindrical member 12, while the outer surface 46 of the transparent housing member 38 faces the external environment.

The first and the second ends 48, 50 of the transparent housing member 38 are provided with inwardly facing annular coupling flanges 56, 58, extending from the cylindrical wall 42, which contact and are secured to the outer surface 20 of the cylindrical member 12 with the elastomeric sleeve 28 secured therebetween. As such, the cylindrical wall 42 of the transparent housing member 38 is spaced from the outer surface 20 of the cylindrical wall 16 of the cylindrical member 12 defining a central cavity 60. The central cavity 60 is defined by the inner surface 44 of the cylindrical wall 42, the inwardly facing annular coupling flange 56 at the first end 48 of the transparent housing member 38, the inwardly facing annular coupling flange 58 at the second end 50 of the transparent housing member 38, and the outer surface 20 of the cylindrical wall 16. It is within this central cavity 60 that the elastomeric sleeve 28 extends outwardly during operation of the present angioplasty pressure transducer 10.

Figure 3:
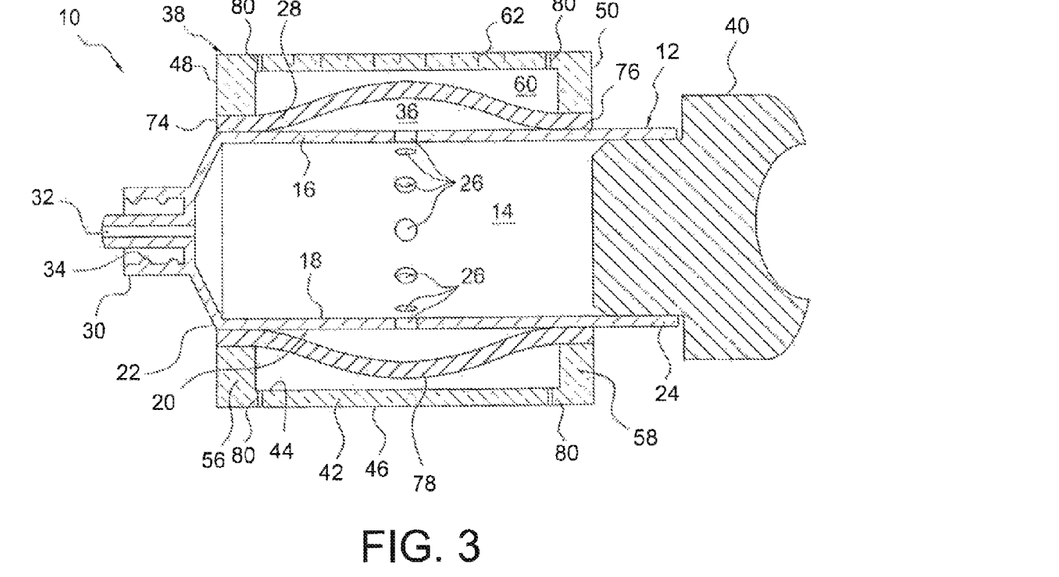
FIGS. 3 and 4 are cross sectional views along the line 2-2 of the angioplasty pressure transducer shown in FIG. 1, with the application of moderate and extensive pressure as discussed below.
Figure 4:
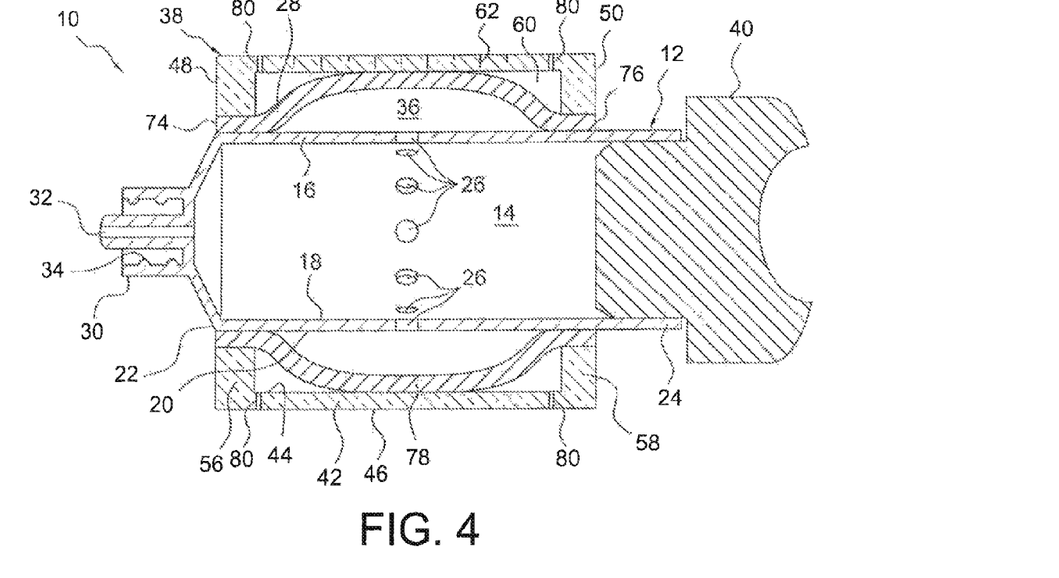

In practice, and when the angioplasty pressure transducer 10 is pressurized during a procedure, the elastomeric sleeve 28 of the angioplasty pressure transducer 10 will deflect outwardly away from the outer surface 20 of the cylindrical wall 16 of the cylindrical member 12 as the space between the elastomeric sleeve 28 and the outer surface 20 of the cylindrical member 12 fills with fluid being forced from the inner cavity 14 of the cylindrical member 12 and through the apertures 26 formed in the cylindrical wall 16 of the cylindrical member 12. Referring to FIGS. 2, 3 and 4, as the elastomeric sleeve 28 expands into the radial central cavity 60 defined by the transparent housing member 38, it will gradually contact the inner surface 44 of the transparent housing member 38 which contains a graduated scale 62 for measuring the magnitude of the pressure in the angioplasty pressure transducer 10 by noting the length of the contact between the elastomeric sleeve 28 and the transparent housing member 38.

Figure 5:
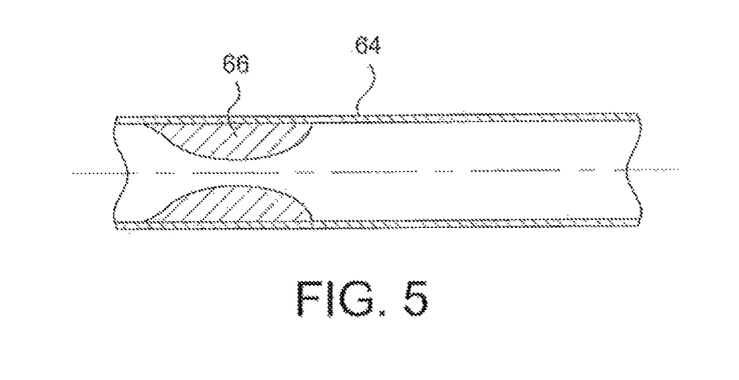
FIGS. 5 through 9 show the steps associated with use of the present angioplasty pressure transducer.
Figure 6:
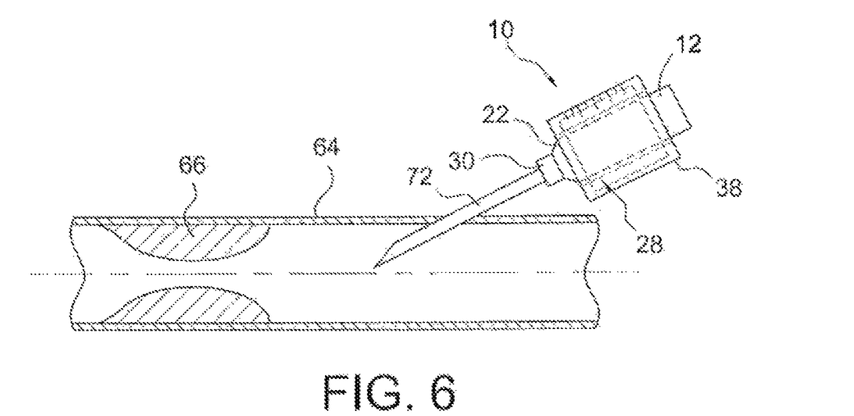

Operation of the present angioplasty pressure transducer 10 is described with reference to FIGS. 5 to 9. Referring to FIG. 5 a blood vessel 64 with a vascular stenosis 66 is disclosed. FIG. 6 shows the angioplasty pressure transducer 10 with die stopper 40 removed, inserted in the blood vessel 64 by puncturing the blood vessel 64 with a needle 72 secured to the fluid port 30 at the first end 22 of the cylindrical member 12. With the stopper 40 removed, access to the blood vessel 64 is facilitated permitting positioning of a guide wire 68 and catheter 70 as described below. Once properly positioned, a guide wire 68 is inserted through the angioplasty pressure transducer 10 and out the fluid port 30. The guide wire 68 is then passed within the blood vessel 64 to a desired location at a position upstream of the vascular stenosis 66. See FIG. 7.

Figure 7:
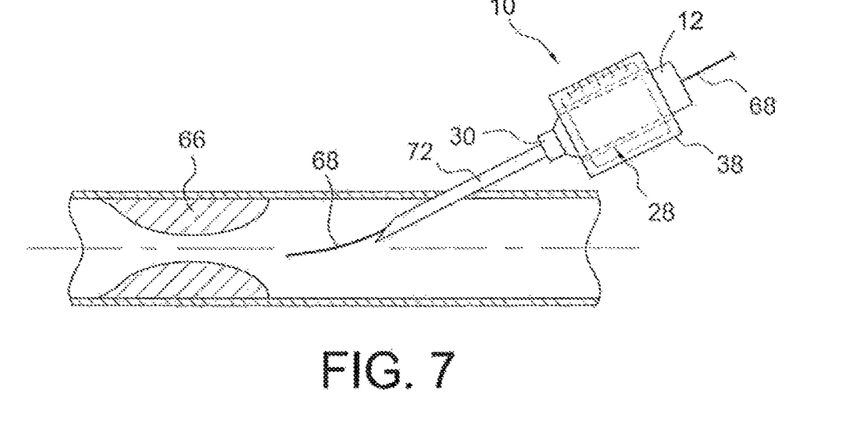
Figure 8:
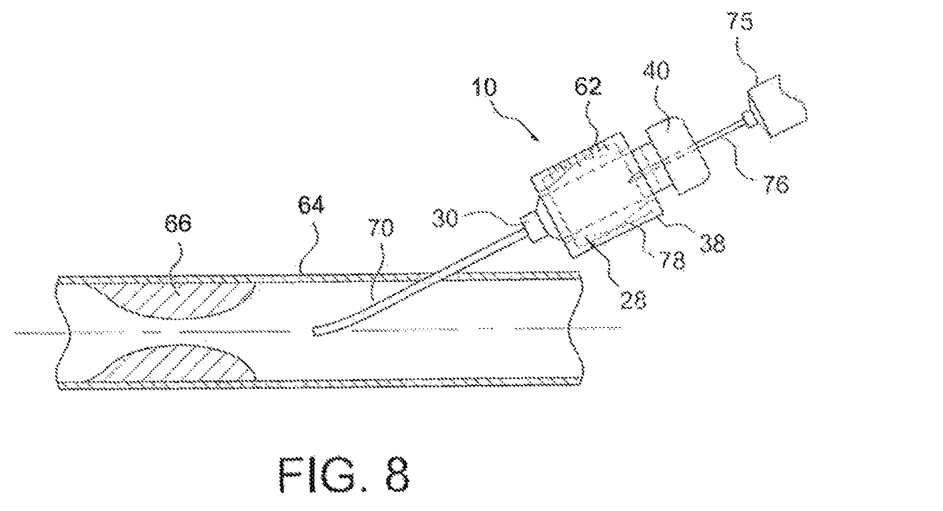

In the time between the step shown in FIG. 7 and the step shown in FIG. 8, the angioplasty pressure transducer 10 (in particular, the needle 72) has been pulled out of the blood vessel 64 over the guide wire 68, leaving the guide wire 68 inside the blood vessel 64. The needle 72 previously secured to the fluid port for the purpose of gaining access to the blood vessel 64 is removed. A catheter 70 is inserted over the guide wire 68 and into the blood vessel 64. The guide ware 68 is then removed from the body. The angioplasty pressure transducer 10 is then connected via the fluid port 30 to the exposed end of the catheter 70.

Referring now to FIG. 8, the stopper 40 of the angioplasty pressure transducer 10 is secured to the second end 24 of the cylindrical member 12 after the angioplasty transducer is properly filled with saline. A suitable, standard syringe 75, with attached needle 76, is then inserted through the stopper 40 of the angioplasty pressure transducer 10. It is appreciated proper venting procedures must be followed to bleed the air out of the system before beginning the angioplasty procedure.

With the configuration shown in FIG. 8, comparative pressure measurements can be made by injecting saline from the syringe 75, through, and filling the cavity 14 of, the angioplasty pressure transducer 10 into the blood vessel 64 before and after percutaneous transluminal angioplasty (PTA). A significant drop in pressure signifies successful angioplasty. Based on the resistance to flow through the angioplasty pressure transducer 10, the volume 36 will deflect the elastomeric sleeve 28 as shown in FIGS. 3 and 4 so that the contact between the elastomeric sleeve 28 and the transparent housing member 38 will display the magnitude of the pressure in the blood vessel 64 before and after PTA. A significant drop in pressure signifies successful angioplasty. It should be noted that the initial contact between the elastomeric sleeve 28 and the transparent housing member 38, when viewed in an axial plane through the angioplasty pressure transducer 10, will appear as a point. As the pressure in the angioplasty pressure transducer 10 increases, the contact between elastomeric sleeve 28 and the transparent housing member 38 gradually progresses to a line contact. The length of the contact line is a measure of the pressure in the angioplasty pressure transducer 10.

As shown in FIGS. 2, 3 and 4, air bleed holes 80 are spaced circumferentially close to the fixed portion of the elastomeric sleeve 28 in the corners of the transparent housing member 38 to prevent trapping air in the inside corners of the first and second ends 48 and 50 of the transparent housing member 38 as the pressure in the angioplasty pressure transducer 10 increases. The pressure on the outer surface of the elastomeric sleeve 28 should be atmospheric to achieve maximum contact between the elastomeric sleeve 28 and the inner surface 44 of the cylindrical wall 42 along the graduated scale, or calibrated region, 62 of the transparent housing member 38.

It should be understood that, as with all measurement devices, the scale markings on the graduated scale 62 of the transparent housing member 38 are applied at the time of manufacture so that actual pressure readings are attainable, if desired.

Measurement of the pressure in the fluid of vessel is objectively determined by measuring the length of the line of contact between the elastomeric sleeve 28 and the transparent housing member 38 of the present angioplasty pressure transducer 10. As briefly mentioned above, the transparent housing member 38 is provided with a calibrated graduated scale 62 so that actual pressures may be obtained, if desired. However, for gross changes in pressure, such as that due to a stenosis/no stenosis condition, the actual pressure reading is not necessary. A long contact length (that is, line of contact between the elastomeric sleeve 28 and the transparent housing member 38) indicates an existing stenosis. A significant reduction in the length of the line of contact between the elastomeric sleeve 28 and the transparent housing member 38 indicates a significant decrease in stenosis and/or hemodynamic improvement.

Figure 9:
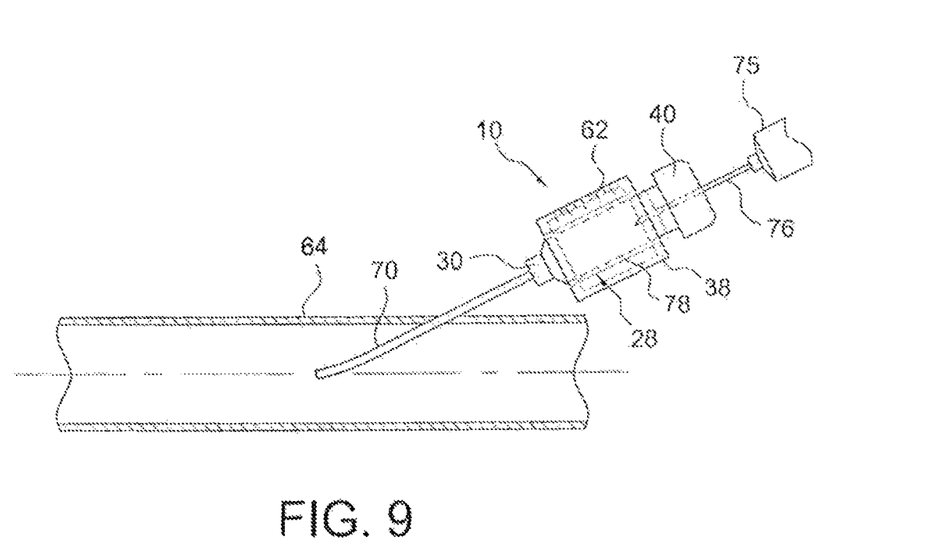

To determine the actual pressure resulting from a stenosis, the operational configurations shown in FIGS. 8 and 9 are used. Before an angioplasty is performed, a pressure value is determined by injecting saline into the stenosed blood vessel 64 and noting the length of elastomeric sleeve 28 in contact with the inner surface 44 of the transparent housing member 38 of the angioplasty pressure transducer 10. A "no contact" region between the elastomeric sleeve 28 and the inner surface 44 of the transparent housing member 38, as shown in FIG. 3, merely means that the pressure sensed by the angioplasty pressure transducer 10 is below the minimum value used in the calibration of the angioplasty pressure transducer 10. The minimum value could be, for example, the pressure required to expel the saline solution through the angioplasty pressure transducer when no restriction to fluid flow exists other than that developed when expelling the saline solution through the catheter into the atmosphere. After angioplasty is performed, a second pressure reading is taken in a similar fashion. A significant reduction in the post-angioplasty pressure reading signifies a hemodynamically significant angioplasty result.

The theoretical background for the angioplasty pressure transducer is given in "Practical Stress Analysis in Engineering Design" by R. Huston & H. Josephs, which is incorporated herein by reference (and relevant pages pp. 529-530), which describes the dilation, i.e., the radial growth, δ of a cylinder with closed ends subjected to internal pressure. The "cylinder" in the angioplasty pressure transducer is the elastomeric sleeve of the device. Both ends of the elastomeric sleeve are essentially closed since they are secured to the outer surface of the cylindrical member and are not free to deform radially when subjected to the pressure of the saline solution. Due to the closed ends of the elastomeric sleeve, the radial deformation adjacent to the closed ends is nonlinear. "Practical Stress Analysis in Engineering Design" shows that between the two nonlinear closed ends spaced at a distance, L, exists a region of constant radial deformation, δ, given by the following equation:

$$\delta := \frac{P \cdot D \cdot (2-v) \cdot (1+k)^2}{16 \cdot E \cdot (1-k)} \quad (1)$$

Where:
L=Length of the elastomeric sleeve between closed ends, inches
P=Internal pressure, psi
D=Outer diameter of the unloaded cylindrical, elastomeric sleeve, inches
d=Inner diameter of the unloaded, cylindrical, elastomeric sleeve, inches
k=d/D
E=Elastic modulus of the elastomeric tube, psi
v=Poissons' ratio Equation 1 was plotted as δ(d) vs. d for the input parameters shown at the top of FIG. 10 to show the influence of the elastomer's wall thickness on radial growth in the region of constant dilation.

Figure 11:
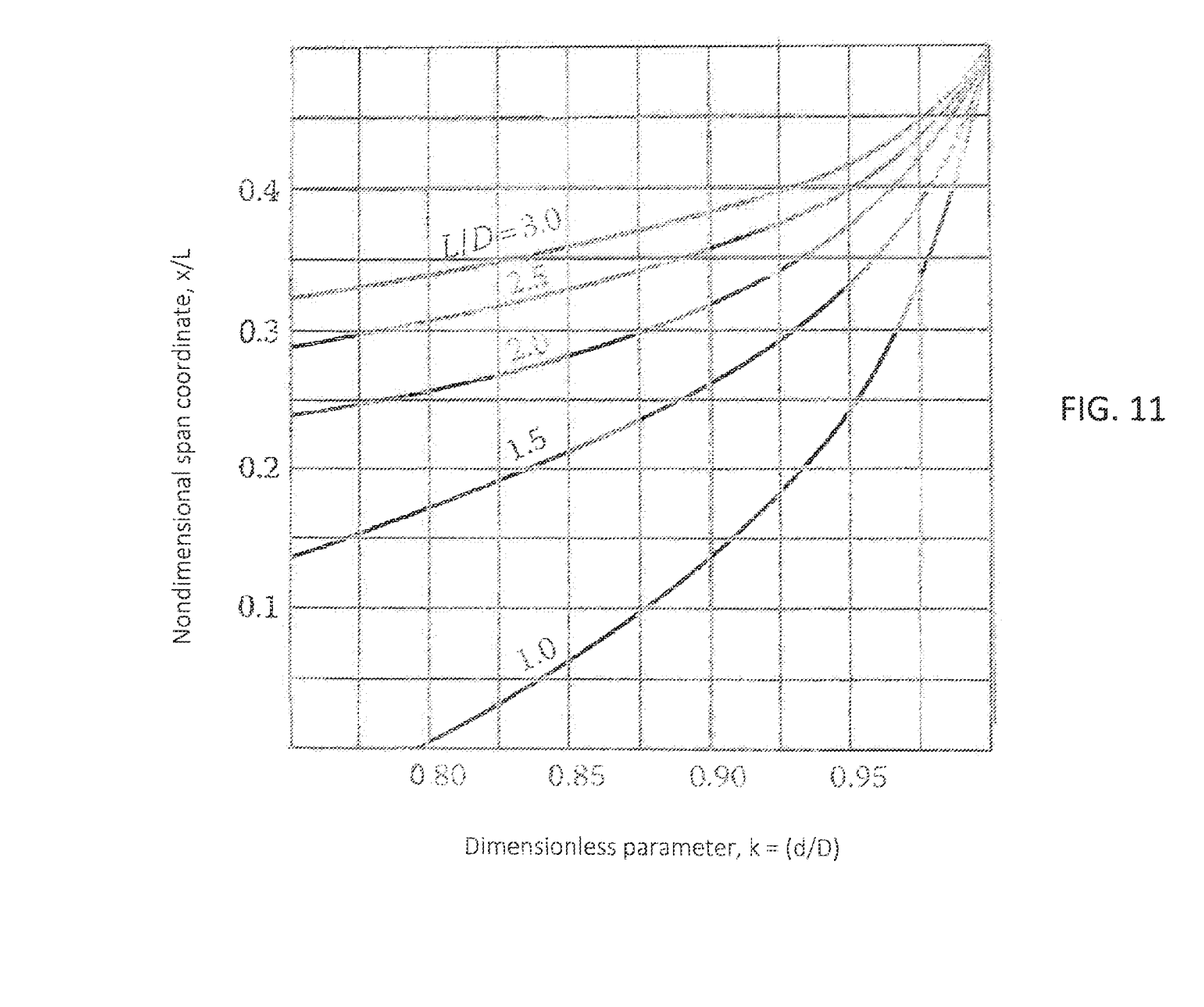

"Practical Stress Analysis in Engineering Design" by R. Huston & H. Josephs shows an experimentally determined design chart for obtaining the length of the region of uniform radial growth, x. Based on two dimensionless quantities, namely, L/D and d/D, the ratio x/L can be determined. The design chart is shown in FIG. 11. The length of the region of uniform radial growth, away from the nonlinear regions at both ends of the elastomeric sleeve is designated as "x". For the design of the angioplasty pressure transducer 10, the required value of x is x=0 since only the nonlinear portions are used to develop the pressure indicating contact region between the elastomeric sleeve and the inner wall of the transparent housing member. Hence, for the angioplasty pressure transducer 10, a value of x=0 was selected for the design.

Figure 10:
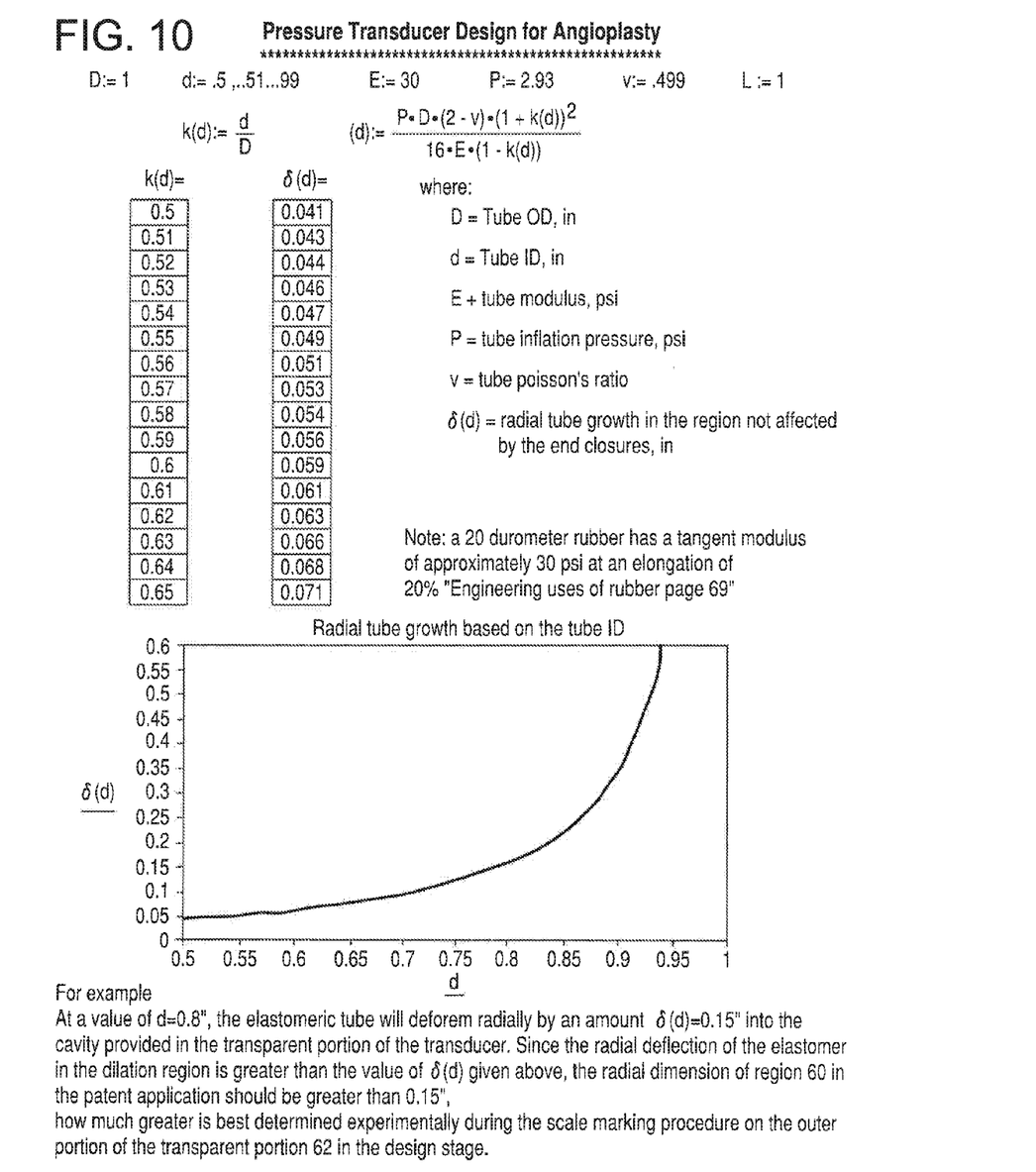
FIGS. 10 and 11 are graphs showing operational characteristics of the present angioplasty pressure transducer.

As an example of the use of Equation 1 and the design chart, refer to FIGS. 10 and 11. The input parameters are given at the top of FIG. 10. The outer diameter, D, of the elastic sleeve is 1 inch. The inner diameter, d, is varied from 0.5 inches to 0.99 inches. The elastic modulus, E, was selected as 30 psi. The fluid pressure, P, of the saline was selected as 2.93 psi and Poissons' ratio was taken as 0.499.

As noted above, we want to eliminate the region of constant dilation, x, completely, in order to obtain a gradually increasing contact length of the elastomeric sleeve with the transparent housing member with increasing pressure. If we select a value of L=1 inch for the length of the elastomeric sleeve between closed ends, our ratio values from FIG. 11 are L/D=1.0, d/D=0.8, x/L=0. Hence, for the angioplasty pressure transducer 10 design in FIG. 10 we obtain the following:
L=1" D=1" d=0.8" and x=0"
which should yield an elastomeric dilation curve having no region of constant dilation. Hence, as the pressure in the saline solution increases, the nonlinear dilation curve will show the required increasingly larger contact with the transparent housing member of the angioplasty pressure transducer 10.

From the dilation curve in FIG. 10, we obtain a value of δ(d)=0.15 inch for d=0.8 inch. Hence, the radially void section above the elastomeric sleeve should be approximately 3/16 of an inch or greater depending on the elastic modulus, E, of the elastomeric portion, which can be determined experimentally. The radially void section is the hollow cylindrical region, or central cavity, 60 as shown in FIG. 2. The inner radius of the hollow cylindrical surface is the outer surface of the elastomeric portion 78. The outer radius of the hollow cylindrical surface is the inner surface 44 of the cylindrical wall 42. The radially void section geometry and pressure scale markings may be determined experimentally.

In an alternate embodiment, the syringe portion and the transducer portion above may be fabricated as an integral unit.

While the preferred embodiments have been shown and described, it will be understood that therein is no intent to limit the invention by such disclosure, but rather, is intended to cover all modifications and alternate constructions falling within the spirit and scope of the invention.

The invention claimed is:

1. An angioplasty pressure transducer, comprising:
a cylindrical member composed of a substantially rigid plastic, the cylindrical member defining an inner cavity, the cylindrical member includes a cylindrical wall having an inner surface and an outer surface, as well as a first end and a second end, the first end of the cylindrical member being provided with a fluid port allowing the passage of fluid into and out of the cylindrical member due to pressure changes in physiological fluid being monitored, the fluid port also including a coupling mechanism for selective attachment of a cannula thereto;
a cylindrical elastomeric sleeve surrounding the cylindrical member such that the cylindrical elastomeric sleeve is wrapped about the outer surface of the cylindrical member;
a cylindrical, transparent housing member positioned about the cylindrical member such that a substantial portion of the outer surface of the cylindrical member, as well as the elastomeric sleeve, are enclosed and encased within the housing member;
the cylindrical wall includes a plurality of small apertures spaced about the circumference of the cylindrical wall at a position substantially located at the longitudinal center of the cylindrical member, the apertures permitting pressurized fluid to pass between the inner cavity and the outer surface of the cylindrical member for expansion of the elastomeric sleeve such that contact between the transparent housing member and the elastomeric sleeve varies based upon applied pressure.

2. The angioplasty pressure transducer according to claim 1, wherein the cylindrical member further includes a removable stopper at the second end thereof, the removable stopper being composed of a resilient material that will reseal after a needle is removed therefrom.

3. The angioplasty pressure transducer according to claim 1, wherein the fluid port includes a central passageway for permitting fluid communication between the inner cavity of the cylindrical member and the external environment.

4. The angioplasty pressure transducer according to claim 1, further comprising, a stopper shaped and dimensioned for frictionally mounting within an opening at the second end of cylindrical member.

5. The angioplasty pressure transducer according to claim 1, wherein the elastomeric sleeve provides a barrier for the passage of fluid from within the inner cavity and creates an external cavity, or volume, into which fluid passes when pressure within the inner cavity forces the fluid through the apertures formed in the cylindrical wall of the cylindrical member and into the external cavity as defined by the outer surface of the cylindrical member and the elastomeric sleeve.

6. The angioplasty pressure transducer according to claim 5, wherein the elastomeric sleeve is a resilient, cylindrical member.

7. The angioplasty pressure transducer according to claim 6, wherein the elastomeric sleeve is shaped and dimensioned to fit snugly about the outer surface of the cylindrical member when no pressure is being applied.

8. The angioplasty pressure transducer according to claim 6, wherein the elastomeric sleeve includes an open first end and an open second end with a central segment connecting the first end and the second end.

9. The angioplasty pressure transducer according to claim 8, wherein the first end of the elastomeric sleeve is coupled to the outer surface of the cylindrical member adjacent the first end of the cylindrical member and the second end of the elastomeric sleeve is coupled to the outer surface of the cylindrical member adjacent the second end of the cylindrical member.

10. The angioplasty pressure transducer according to claim 9, wherein the central segment of the elastomeric sleeve is not secured to the outer surface of the cylindrical member.

11. The angioplasty pressure transducer according to claim 1, wherein the transparent housing member includes a cylindrical wall having an inner surface and an outer surface, the transparent housing member also includes a first end and a second end, wherein the inner surface of the transparent housing member faces the elastomeric sleeve and outer surface of the cylindrical wall of the cylindrical member, while the outer surface of the transparent housing member faces the external environment.

12. The angioplasty pressure transducer according to claim 11, wherein the elastomeric sleeve is a resilient, cylindrical member.

13. The angioplasty pressure transducer according to claim 12, wherein the first end of the transparent housing member is provided with an inwardly facing annular coupling flange and the second end of the transparent housing member is provided with inwardly facing annular coupling flange, the inwardly facing annular coupling flanges extending from the cylindrical wall of the transparent housing member, wherein the inwardly facing annular coupling flanges contact and are secured to the outer surface of the cylindrical member with the elastomeric sleeve secured therebetween.

14. The angioplasty pressure transducer according to claim 13, wherein the cylindrical wall of the transparent housing member is spaced from the outer surface of the cylindrical wall of the cylindrical member defining a cavity that is defined by the inner surface of the cylindrical wall of the transparent housing member, the inwardly facing annular coupling flange at the first end of the transparent housing member, the inwardly facing annular coupling flange at the second end of the transparent housing member, and the outer surface of the cylindrical wall of the cylindrical member.

15. The angioplasty pressure transducer according to claim 1, wherein the transparent housing member includes air bleed holes to prevent trapping air in the inside of the transparent housing member as the pressure in the angioplasty pressure transducer increases.

16. The angioplasty pressure transducer according to claim 1, wherein the transparent housing member is provided with a calibrated graduated scale.

17. An angioplasty pressure transducer, comprising:
a cylindrical member composed of a substantially rigid plastic, the cylindrical member defining an inner cavity, the cylindrical member includes a cylindrical wall having an inner surface and an outer surface, as well as a first end and a second end, the first end of the cylindrical member being provided with a fluid port allowing the passage of fluid into and out of the cylindrical member due to pressure changes in physiological fluid being monitored;

a cylindrical elastomeric sleeve surrounding the cylindrical member such that the cylindrical elastomeric sleeve is wrapped about the outer surface of the cylindrical member;

a cylindrical, transparent housing member positioned about the cylindrical member such that a substantial portion of the outer surface of the cylindrical member, as well as the elastomeric sleeve, are enclosed and encased within the housing member, the transparent housing member including apertures for venting purposes, the transparent housing member also including a cylindrical wall having an inner surface and an outer surface, the transparent housing member also includes a first end and a second end, wherein the inner surface of the transparent housing member faces the elastomeric sleeve and outer surface of the cylindrical wall of the cylindrical member, while the outer surface of the transparent housing member faces the external environment, the first end of the transparent housing member is provided with an inwardly facing annular coupling flange and the second end of the transparent housing member is provided with inwardly facing annular coupling flange, the inwardly facing annular coupling flanges extending from the cylindrical wall of the transparent housing member, the inwardly facing annular coupling flanges contact and are secured to the outer surface of the cylindrical member with the elastomeric sleeve secured therebetween;

the cylindrical wall of the cylindrical member includes a plurality of small apertures spaced about the circumference of the cylindrical wall of the cylindrical member at a position substantially located at the longitudinal center of the cylindrical member, the apertures permitting pressurized fluid to pass between the inner cavity and the outer surface of the cylindrical member such that the volume of a cavity defined by the outer surface of the cylindrical wall and the elastomeric sleeve will vary depending upon the pressure of fluid being forced from within the inner cavity and the contact between the transparent housing member and the elastomeric sleeve varies based upon applied pressure.

* * * * *